United States Patent [19]

Aldridge

[11] Patent Number: 5,351,340

[45] Date of Patent: Oct. 4, 1994

[54] WORK GARMENT WITH LUMBAR SUPPORT

[75] Inventor: Donald Aldridge, New Carlisle, Ohio

[73] Assignee: Lion Apparel, Inc., Dayton, Ohio

[21] Appl. No.: 911,276

[22] Filed: Jul. 9, 1992

Related U.S. Application Data

[63] Continuation-in-part of Ser. No. 780,151, Oct. 21, 1991, Pat. No. 5,157,790.

[51] Int. Cl.$^5$ .............................................. A41D 1/02
[52] U.S. Cl. ........................................ 2/108; 2/81; 2/221; 2/227; 2/236; 2/255; 2/338
[58] Field of Search ........................... 2/2, 69, 79, 81, 82, 2/108, 227, 229, 230, 231, 234, 235, 236, 237, 255, 256, 44, 92, 102, 220, 221, 300, 311, 338; 450/103, 143, 155; 602/13, 19

[56] References Cited

U.S. PATENT DOCUMENTS

| | | | |
|---|---|---|---|
| 2,335,971 | 12/1943 | Scholle | 2/221 |
| 2,372,034 | 3/1945 | Versoy | 128/96 |
| 2,501,900 | 3/1950 | Herbener | 2/255 |
| 2,815,023 | 1/1955 | Hammersley | 128/99 |
| 2,977,601 | 4/1961 | Winston | 2/221 |
| 3,141,457 | 7/1963 | Davidson | 128/95 |
| 3,422,461 | 1/1969 | Froehlich | 2/255 |
| 4,022,197 | 5/1976 | Castiglia | 128/101 |
| 4,143,663 | 3/1979 | Williams | 450/103 |
| 4,627,109 | 12/1986 | Carabelli | 2/300 |
| 4,794,916 | 11/1986 | Porterfield et al. | 128/78 |
| 4,976,653 | 12/1990 | White | 2/221 |
| 4,991,573 | 3/1990 | Miller | 128/78 |
| 5,036,548 | 8/1991 | Grilliot | 2/227 |
| 5,046,488 | 9/1991 | Schiek | 2/338 |
| 5,050,244 | 9/1991 | Kleinman | 2/227 |
| 5,105,474 | 4/1992 | Skinner | 2/69 |
| 5,127,108 | 7/1992 | Weiss | 2/236 |
| 5,157,790 | 10/1992 | Aldridge | 2/81 |

FOREIGN PATENT DOCUMENTS

2501974  9/1982  France ................................ 2/108

Primary Examiner—Clifford D. Crowder
Assistant Examiner—Diana L. Biefeld
Attorney, Agent, or Firm—Thomson, Hine and Flory

[57] ABSTRACT

A work garment having a waist portion covering a lower back area of a wearer and a front closure, and a support member, attached to the garment, for supporting a lumbar region of the wearer. The support member preferably includes a plurality of elastic bands extending about the waist portion of the garment and having complementary closure members positioned adjacent to the front closure of the work garment, and a contact member, attached to the elastic straps, positioned to contact the lumbar region of the wearer. In one embodiment, the elastic straps are integral with the work garment, which may be a coverall, and in other embodiments with firefighter garments such as a jacket, pant, and girdle. In one embodiment, the contact member consists of a resilient pad centered in the lumbar area of the wearer, and in another embodiment, the contact member consists of a plurality of elongate, vertically-extending stays.

8 Claims, 5 Drawing Sheets

WORK GARMENT WITH LUMBAR SUPPORT

RELATED APPLICATION INFORMATION

This application is a continuation-in-part of U.S. application Ser. No. 07/780,151 filed Oct. 21, 1991 now U.S. Pat. No. 5,157,790.

BACKGROUND OF THE INVENTION

The present invention relates to work garments and, more particularly, garments having orthopedic components for reducing the strain of a wearer when encountering heavy loads.

Many work-related activities require a worker to lift and carry heavy objects causing strain in the lower back area of the worker. A typical work garment, such as a coverall, provides little means for supporting the lower back area of a worker while performing his duties. The objective of a coverall is rather to provide a barrier between the worker's clothing and the work area to prevent the worker's clothing from being soiled.

A work garment having a particularly specialized application is a firefighter garment. A typical firefighter garment includes a pant and jacket, each having an outer shell of a fire-resistant aramid fiber such as NOMEX or KEVLAR (NOMEX and KEVLAR are trademarks of E. I. Dupont de Nemours & Co., Inc.) and an inner liner having a moisture barrier component and a thermal barrier component. The moisture barrier may be GORTEX material (GORTEX is a trademark of W. L. Gore & Associates, Inc.) and the thermal barrier may be a felt of aramid fibers. The inner liner components typically are quilted together, and the inner liner is separable from the outer shell to facilitate laundering of the garment.

The firefighter pant typically is beltless and is held in position by suspenders which fit under the jacket. The inner pant liner and outer pant shell snap or button together and the suspender ends or tabs may attach to such buttons or snaps, or may be attached by separate means. Both the jacket and the pant are loose fitting and somewhat baggy to allow freedom of movement.

While such firefighter garments provide adequate protection against such hazards as heat, water and flash flame, they, like conventional work garments, provide no protection for the hazard of muscle strain, especially in the lumbar region of the spine of the wearer. In the fighting of fire, the firefighter is called upon to carry heavy equipment such as hoses and ladders, over his shoulder, and occasionally is required to carry an injured person over his shoulder in the well-known "firemen's carry" maneuver. In addition, the firefighter often carries a tank of breathing air strapped to his back. All of these items and activities impose a stress upon the lumbar region of the back which is often an unbalanced imposition of a weight load.

While there are many types of designs for so-called lumbar stabilizers, such as the stabilizer disclosed in Porterfield, et al. U.S. Pat. No. 4,794,916 and Miller U.S. Pat. No. 4,991,573, such devices are designed to provide comfort and reduce stress to an individual who has sustained an injury in the lumbar area of the spine. It is not an object of such devices to provide a prophylactic benefit to a wearer in a typical work environment or in the hazardous environment of a firefighter. Further, such devices are designed to be worn independently of any other type of garment and typically are worn underneath the outer garments of a wearer.

It is impractical to require workers and firefighters to keep track of and separately put on such lumbar stabilizers, in addition to other garments and gear, in day-to-day work activities or in the rush to answer an alarm. Accordingly, there is a need for a work garment which provides support for a worker in the lumbar region of the wearer's spine in order to minimize the risk of injury to that region sustained during strenuous work activity.

SUMMARY OF THE INVENTION

The present invention is a work garment with a support which minimizes the stress imposed upon the lumbar region of the spine of the wearer, thereby reducing the likelihood of spinal and muscle injury to workers who must lift or carry heavy loads in the course of their work activities. The support is integral with the garment and can be selectively activated and deactivated so that the support feature is applied only when needed. Another benefit of the invention is the so-called "placebo effect," wherein the mere presence of the invention in a work garment makes the wearer self-conscious of his lifting form, and thereby serves to encourage use of good lifting form.

In one preferred embodiment of the invention, the garment is a coverall having a waist portion coverinq the lower back area of the wearer, including the lumbar region, and a support member, attached to the inside surface of the coverall for supporting the lumbar region of the wearer. The support member includes a plurality of elastic bands which encircle the waist of the wearer and includes a closure mechanism in the front of the wearer adjacent to the coverall closure. The elastic bands support a contact member positioned adjacent the lumbar region of the spine, which ensures proper alignment of the lumbar vertebrae during bending and lifting. The contact member is a resilient pad positioned over the lumbar vertebrae.

The closure member of the elastic bands allows the wearer to activate the support member by connecting the closure member, thereby applying a radially inward pressure against the lumbar region, or deactivate the support member by disconnecting the closure member to relax the elastic bands. Accordingly, the support member can be worn comfortably at all times and activated only when needed during strenuous work activity.

In an alternate embodiment of the invention, the garment is a firefighter pant having an inner liner with a thermal layer and an outer shell having a waist portion covering the lower back area of the wearer, including the lumbar region, and a support member, attached to the shell, for supporting the lumbar region of the wearer. The support member includes a plurality of elastic bands which encircle the waist of the wearer and includes a closure mechanism in the front of the wearer adjacent to the pant closure. The elastic bands support a contact member positioned adjacent the lumbar region of the spine, which ensures proper alignment of the lumbar vertebrae during bending and lifting. In one embodiment, the contact member is a pad positioned over the lumbar vertebrae and in another embodiment, the contact member includes a plurality of flexible, elongated stays which extend vertically in parallel with the lumbar vertebrae. The closure member of the elastic bands allows the wearer to activate and deactivate the support member identically to that of the coverall.

In a second alternate embodiment, the support member includes a girdle made of shell material which encloses the waist of the wearer in the lumbar region and includes inner and outer layers in closing the elastic bands. The girdle includes buttons for connecting to suspenders, and button holes or snaps for connection to the firefighter pant, thereby acting as an integral component of the pant suspension system. Such a girdle is therefore retrofittable to existing firefighter pants. The girdle includes a front closure member, separate from the elastic bands, so that the girdle may be worn comfortably at all times, and the elastic bands adjusted activate it when needed.

Other embodiments in which the present invention can be incorporated is a firefighter's jacket, paramedic uniforms, and other work related garments such as overalls. Any garment worn by a worker whose activities involve lifting or strenuous activity which would require lumbar support would be ideal for incorporating the present invention.

In all of the embodiments, it is preferable to provide closure members consisting of complementary strips of hook and loop material. However, other closure members, such as buckles, snaps and hook-and-D connectors may be used.

Accordingly, it is an object of the present invention to provide a work garment with an integral lumbar support mechanism; a work garment with a lumbar support mechanism which can be activated and de-activated easily as needed to ensure wearer comfort at all times; a work garment with integral lumbar support mechanism for a work garment which does not add significantly to the weight of the work garment; and a work garment with a lumbar support mechanism which is relatively inexpensive to incorporate into the garment, or can be provided as an integral component retrofitted to an existing garment design.

Other objects and advantages of the present invention will be apparent from the following description, the accompanying drawings and the appended claims.

DETAILED DESCRIPTION

Figure 1:
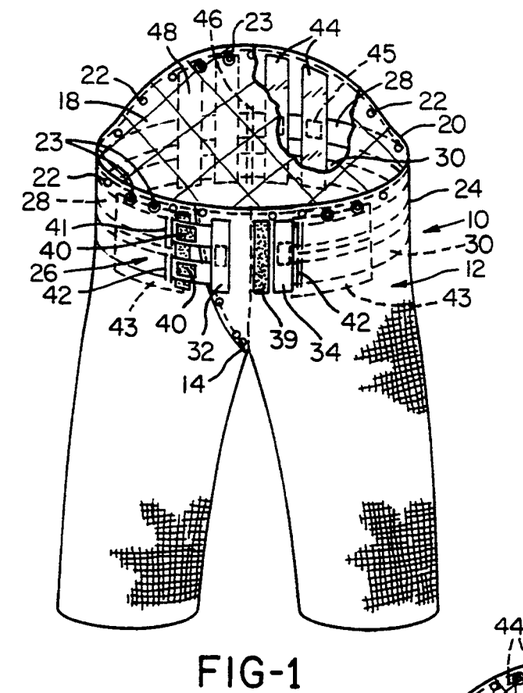
FIG. 1 is a somewhat schematic, perspective view of a first alternate embodiment of the invention showing a firefighter pant embodying the present invention.
Figure 2:
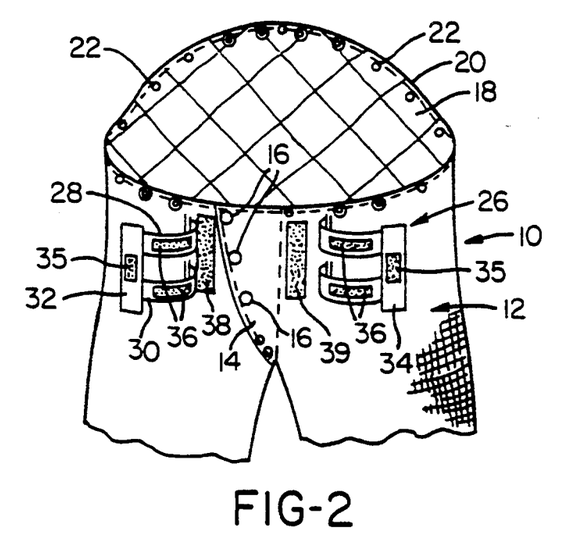
FIG. 2 is a detail of the pant of FIG. 1, showing the underside of the ends of the straps.

As shown in FIGS. 1 and 2, an alternate embodiment of the present invention is a firefighter garment, generally designated 10, which is a pant having an outer shell 12 made of a woven aramid fiber such as NOMEX or KEVLAR. The outer shell includes a front closure 14 which is secured by snaps 16. The pant 10 includes an inner liner 18 having an outer moisture barrier quilted to a batting of NOMEX fibers. The inner liner 18 is shaped to fit within the outer shell 12 and is attached to the outer shell at the waistline by snaps 22. The liner 18 includes suspender buttons 23 which protrude through the shell 12.

The waist portion 24 of the garment includes a support member, generally designated 26. The support member includes upper and lower elastic straps 28, 30, respectively. The waist portion 24 and support member 26 are positioned on the pant 10 to encircle the midriff of a wearer, and the rear portion of the support member is positioned to lie adjacent to the lumbar region of the spine of the wearer.

Adjacent ends of the straps 28, 30 are connected by closure tabs 32, 34, and each of the tabs has attached to its underside a hook component 35 of a hook and loop closure mechanism. Similarly, straps 28, 30 include strips 36 of hook material. The outer shell 12 includes complementary strips 38, 39 loop material, and the outer surfaces of the straps 28, 30 adjacent tabs 32, 34 include squares 40 of loop material (see also FIG. 4).

The straps 28, 30 extend through slits 41, 42 formed in the outer shell which, at the waist portion 24, includes inner retainer squares 43 of shell material stitched to the outer shell. The portions of straps 28, 30 extending between slits 41, 42 extend between the squares 43 and shell 12. The straps 28, 30 support a plurality of oblong, vertically-extending stays 44, secured by hook and loop connections 45 to the radially inner surface of the straps. The straps preferably are made of a rigid plastic material such as nylon. The straps 28, 30 are secured to the rear of the waist portion 24 by stitching 46 and the stays 44 are positioned to lie on either side of the lumbar vertebrae of a wearer.

As shown in FIG. 1, the rear portion 48 of the waist portion 24 of the pant 10 is raised, relative to the front portion of the pant, to ensure that a sufficient portion of the lumbar region of the wearer is contacted by the stays 44.

Figure 3:
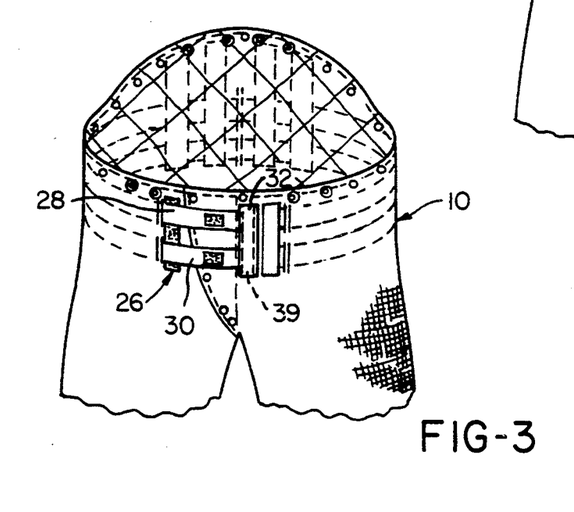
FIG. 3 is a detail of the pant of FIG. 1 showing an end of the support member attached to the pant in the first step of activation.
Figure 4:
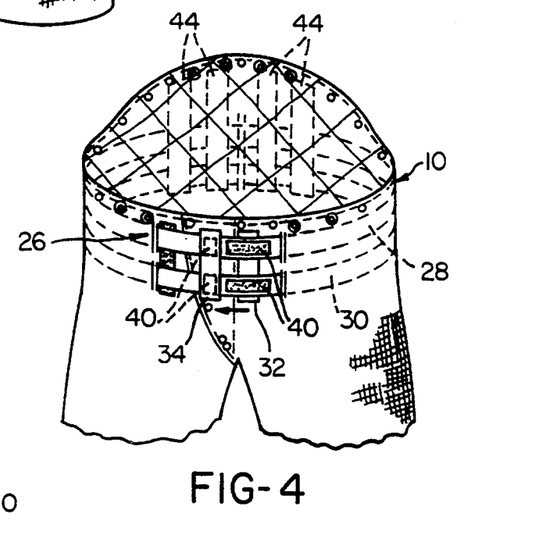
FIG. 4 is the detail of FIG. 3 showing the support member fully activated.

The method of activating the support member 26 is shown sequentially in FIGS. 1, 3, and 4. FIG. 1 shows the support member in a de-activated configuration; that is, the tabs 32, 34 are not attached to each other and accordingly, the straps 28, 30 do not exert an inward constrictive force on the mid-section of a wearer. Preferably, tabs 32, 34 are attached to panels 38 of loop material adjacent to slits 41, 42 (see FIG. 2).

As shown in FIG. 3, in order to activate the support member 26, tab 32 is brought over to panel 39 so that the panels 35 and/or 36 on tab 32 and/or straps 28, 30 (see FIG. 2) contact panel 39, thereby attaching the tab to the pant 10 at the position of panel 39. Next, as shown in FIG. 4, tab 34 is superposed to squares 40 so that panel 36 on tab 34 is brought into contact with the squares 40 to make a connection and fix the tab 34 relative to the squares. Accordingly, the pant 10 shown in FIG. 4 is in an activated configuration in which the ends of the straps 28, 30 are in an overlapping relation and are tightened about the waist of a wearer, thereby urging the stays 44 into the lower back of the wearer in the lumbar region, preferably on either side of the lumbar vertebrae. This constrictive pressure supports the back of the wearer and reduces the likelihood of back injury due to heavy or unbalanced lifting.

The adjustment of the support member 26 from the activated configuration shown in FIG. 4 to the de-activated configuration shown in FIG. 1 is simply the reverse of the aforementioned steps. The tab 34 is pulled away from the straps 28, 30, thereby separating the hook and loop panels from each other, and the tab is allowed to retract to its normal position. Tab 32 is then separated from the shell 12, thereby separating the hook and loop closure panels on the tab and pant shell 12 at that point, and straps 28, 30 are allowed to retract to their unstretched positions. The tabs 32, 34 then assume the configuration shown in FIG. 1. It is anticipated that a firefighter wearing the pant 10 of the present invention would wear the pant principally in a de-activated configuration, as shown in FIG. 1, then adjust the support member 26 to the activated configuration of FIG. 4 before fighting a fire or engaging in heavy lifting.

Figure 5:
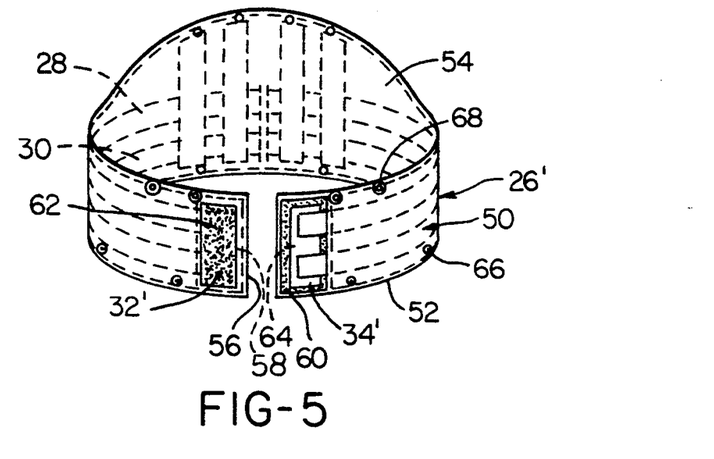
FIG. 5 is a detail of a second alternate embodiment of the invention showing a girdle incorporating the support member.
Figure 6:
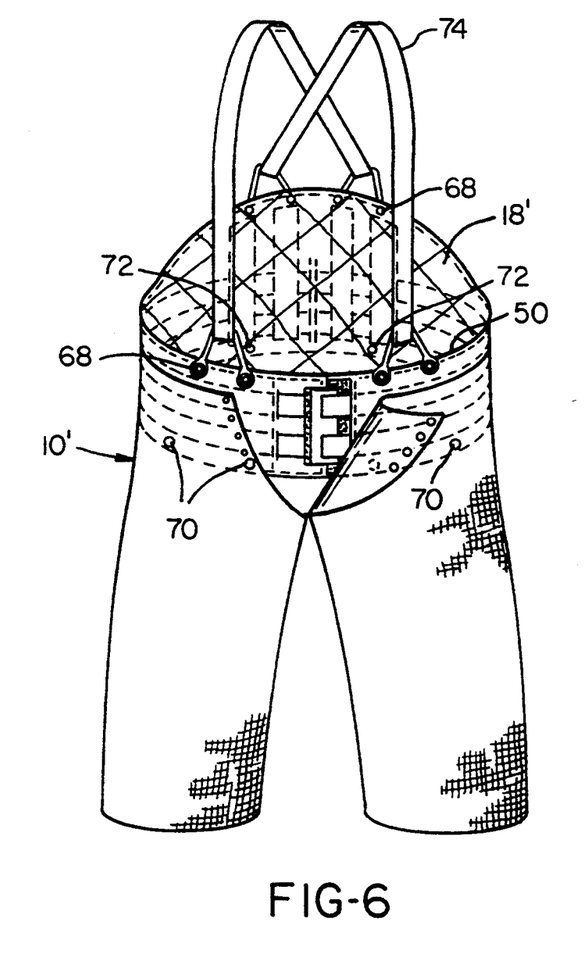
FIG. 6 is the alternate embodiment of the invention of FIG. 4 retrofitted to a pant.

A second alternate embodiment of the invention is shown in FIGS. 5 and 6. In FIG. 5, the support member 26' includes a girdle 50 made of inner and outer layers 52, 54 of shell material stitched together at their peripheries. The girdle 50 includes a front closure 56 which includes complementary panels 58, 60 of hook and loop material to secure the girdle when worn.

The straps 28, 30 are attached at their ends to tabs 32', 34', each of which has a panel of hook and loop material 62, 64 attached to it.

The girdle 50 includes snaps 66 about its lower periphery and suspender buttons 68 attached to about its upper periphery. As shown in FIG. 6, the girdle 50 is attached to a firefighter pant 10' by engagement of the girdle with complementary snaps 70 mounted on the outer shell and complementary snaps 72 mounted on the inner liner 18'. A pair of standard firefighter suspenders 74 are then attached to the buttons 68 of the girdle 50 to complete the pant 10' construction. In order to activate the girdle 50, panel 32' is stretched to contact the exposed portion of panel 58 of the girdle and is attached by means of the hook and loop connection between those components. The tab 34' is then stretched and attached to the back side of tab 32' so that the complementary hook and loop panels of those components engage. When this connection is effected, the stays 44 are urged into the lumbar region of the back of the wearer by the constrictive force of the straps 28, 30.

Figure 7:
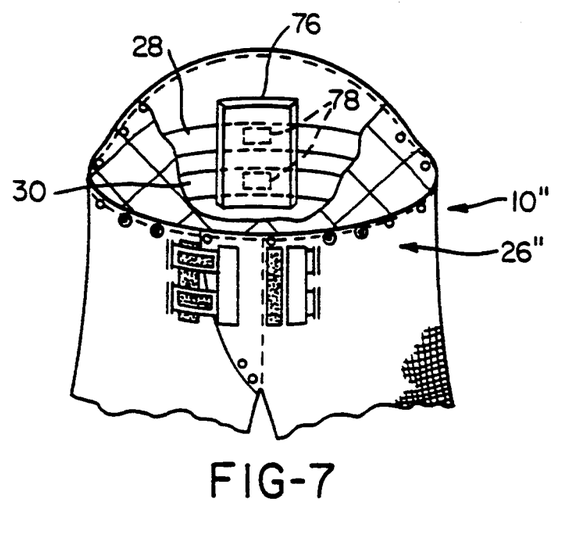
FIG. 7 shows a third alternate embodiment of the invention in which the pant of FIG. 1 has been modified to include a contact pad.

A third alternate embodiment 10" having a modified support member 26" is shown in FIG. 7. In this embodiment, the support member 26" is identical in all respects to the support member 26 of FIGS. 1–4, except that the stays 44 have been replaced by a lumbar pad 76. The lumbar pad 76 is made of a thick, hard foam and is approximately 8 inches long, 6 inches wide, and ½ inch thick. The pad 76 is attached by hook and loop connections 78 to the straps 28, 30 of the support member 26". Accordingly, den the support member 26" of the pant 10" shown in FIG. 7 is activated, the straps 28, 30 urge the pad 76 into the lumbar vertebrae of the wearer to provide support for lifting and bending movement.

Figures 8, 9, 10, 11, 12:
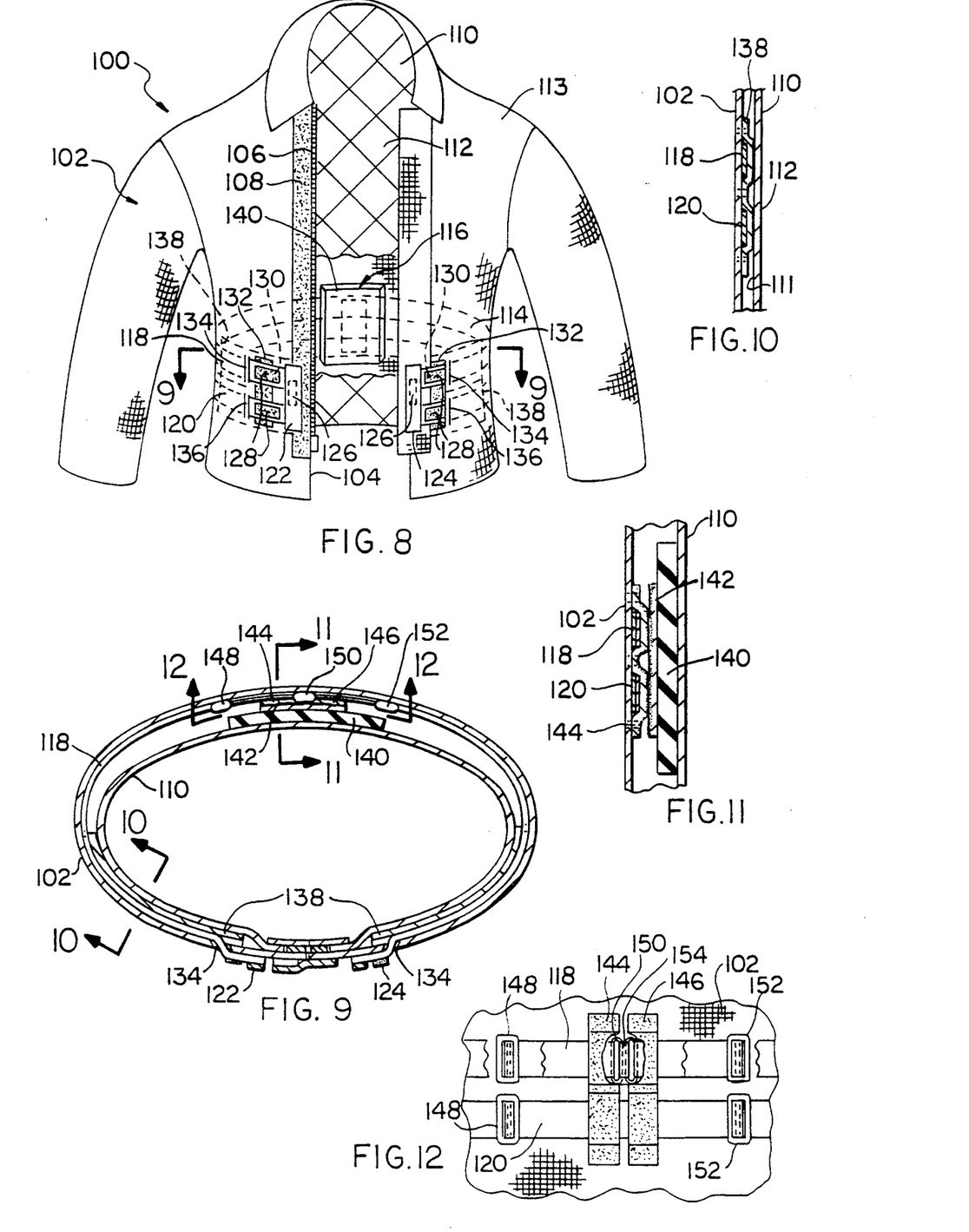
FIG. 8 is a schematic, perspective view of a fourth alternate embodiment of the invention showing a firefighter jacket incorporating the support member.
FIG. 9 is a horizontal cross-sectional view taken along line 9—9 of FIG. 8 showing the support member.
FIG. 10 is a vertical cross-sectional view taken along line 10—10 of FIG. 9 showing the elastic strap means.
FIG. 11 is a vertical cross-section view taken along line 11—11 of FIG. 9 showing the support member.
FIG. 12 is a sectional view taken along line 12—12 of FIG. 9 showing the attachment means for the contact member.

As shown in FIG. 8, a fourth alternate embodiment of the invention is a firefighter jacket 100. The jacket 100 includes an outer shell 102 made of a woven aramid fiber and which includes a front closure 104 secured by a slide fastener 106 and hook and loop closure components 108. The jacket 100 includes an inner liner 110 having an outer moisture barrier 111 (see FIG. 10) attached to a thermal liner 112 of NOMEX material. The inner liner 110 is shaped to fit within the outer shell 102 and is attached to the outer shell along the front closure 104 by snaps (not shown). The jacket 100 includes a torso portion 113 having a waist segment 114 which covers a lower back area of a wearer.

The waist segment 114 of the jacket 100 includes a support member, generally designated 116. The support member includes upper and lower elastic straps 118, 120, respectively. The waist segment 114 and support member 116 are positioned on the jacket 100 to encircle the midriff of a wearer, and the rear portion of the support member is positioned to lie adjacent to the lumbar region of the spine of the wearer.

Adjacent ends of the straps 118, 120 are attachable to each other by closure tabs 122, 124, and each of the tabs has attached to its underside a hook component 126 of a hook and loop closure mechanism. Similarly, straps 118, 120 include strips 128 of hook material attached to their undersides and strips 130 of loop material attached to their outer surfaces. The outer shell 102 includes complementary strips 132 of loop material.

The straps 118, 120 extend through slits 134, 136 respectively, formed in the outer shell 102 which, at the waist segment 114, include inner retainer squares 138 of shell material stitched to the inside surface of the outer shell. Portion of straps 118, 120 between slits 134, 136 extend between the squares 138 and shell 102 as shown in FIGS. 9 and 10.

A lumbar pad 140 made of a thick, hard foam similar to pad 76 in embodiment 10" is located in the back of the waist segment 114 to support the lumbar vertebrae of the wearer. Pad 140 is removably attached to the inside surface of the outer shell 102 by hook and loop fasteners. A hook strip 142 is applied to the back of the pad and two loop strips 144, 146 are stitched to the outer shell. The inner liner 110 covers the front of the lumbar pad 140 (also shown in FIG. 11).

The method of activating the support member 116 is similar to the embodiments of FIGS. 1–7 in that tab 122 brought over the loop strip 132 so that hook strips 126 and/or 130 on tab 122 and/or straps 118, 120 contact loop strip 132, thereby attaching the tab and/or the elastic straps. Next, tab 124 is brought over to hook strips 128 on the upper and lower elastic straps to make a connection and fix the tab 124 relative to the loop strip 132. Accordingly, the jacket is in an activated configuration in which the ends of the straps 118, 120 are in an overlapping relation and are tightened about the waist of a wearer, thereby urging the lumbar pad 140 into the lower back of the wearer in the lumbar region. This constrictive pressure supports the back of the wearer and reduces the likelihood of back injury due to heavy or unbalanced lifting.

The adjustment of the support member 116 from the activated configuration shown in FIG. 9 to the deactivated configuration shown in FIG. 8 is simply the reverse of the aforementioned steps.

Depending upon the waist size of the wearer, the tension of the upper and lower elastic straps 118, 120 may be adjusted. As shown in FIG. 12, the tension in the elastic straps 118, 120 can be adjusted through the incorporation of buckles 148, 150 and 152. Buckles 148 and 152 are attached to straps 118, 120 by looping the end of the strap over the center rung of the buckle and sewing the end over upon itself. Straps 118 and 120 are then threaded through the outside rungs of bucket 150 which is positioned between loop strips 144, 146 by loop 154, which is a portion of outer shell material looped over the center rung of buckles 150 and sewn to outer shell 102. Straps 118, 120, after being threaded through the outer rung of buckles 150, are then directed back toward buckles 148 and 152 and threaded between the outer rungs of buckles 148 and 152 over the center rung. The tension of the straps 118, 120 can then be adjusted by moving buckles 148 and 152 axially along the strap to shorten or lengthen the strap to the desired length.

Figure 13:
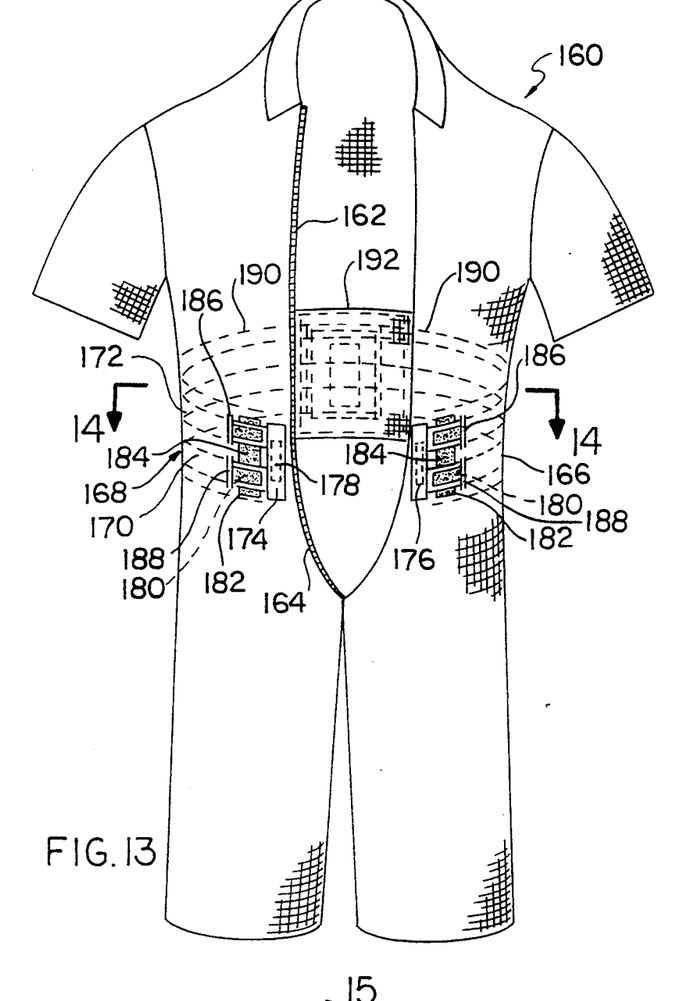
FIG. 13 is a schematic, perspective view of a preferred embodiment of the invention showing a coverall incorporating the support member.

In addition to firefighter garments, any garment worn which involves lifting or strenuous activity and requires lumbar support, particularly work garments, can be modified into the present invention. The preferred embodiment of the invention is shown in FIG. 13 which is a representative work garment known as a coverall 160. Coverall 160 is made of a sturdy cloth material such as cotton, polyester, or a cotton/polyester blend. The coverall 160 includes a front closure 162 which is secured by a slide fastener 164, or alternatively by snaps.

The coverall 160 includes a waist segment 166 wherein the support member 168 is located. The support member 168 is identical to the support member of the previous embodiment and includes upper and lower elastic straps 170, 172, respectively. The waist segment 166 and support member 168 are positioned on the coverall to encircle the midriff of a wearer, and the rear portion of the support member is positioned to lie adjacent to the lumbar region of the spine of the wearer.

Adjacent ends of the straps 170, 172 are connected by closure tabs 174, 176, and each of the tabs has attached to its underside a hook component 178 of a hook and loop closure mechanism. Straps 170, 172 include strips 180 of hook material located on the underside surface of the straps directly underneath strips of loop material 182 located on the outer surface of the straps. The outer surface of the coverall also includes complementary strips 184 of loop material.

Figure 14:
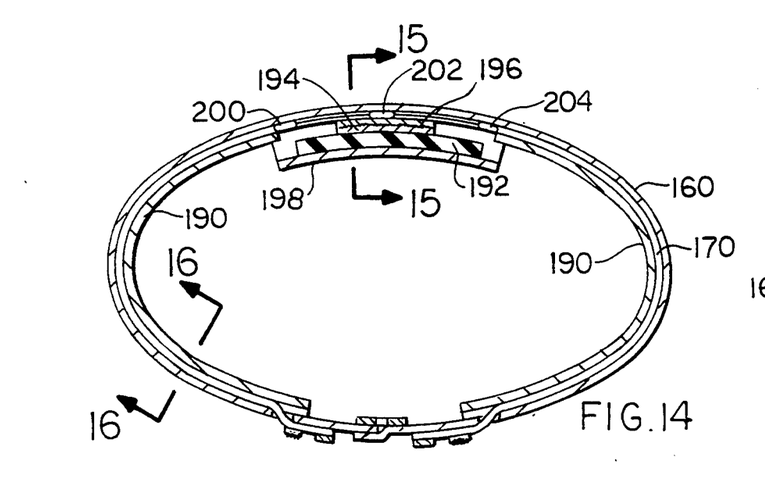
FIG. 14 is a horizontal cross-sectional view taken along line 14—14 of FIG. 13 showing the support member.
Figure 15:
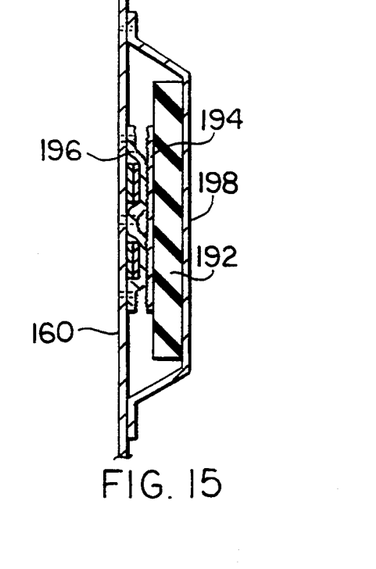
FIG. 15 is a vertical cross-sectional view taken along line 15—15 of FIG. 14 showing the support member.
Figure 16:
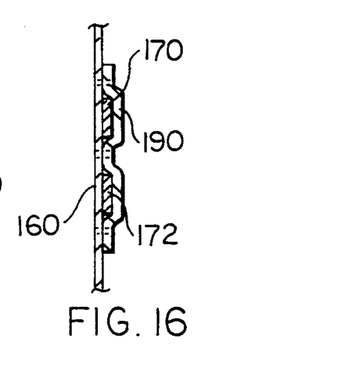
FIG. 16 is a vertical cross-sectional view taken along line 16—16 of FIG. 14 showing the elastic strap means.

The straps 170, 172 extend through slits 186, 188 formed in the coverall 160 which, at the waist portion, includes inner retainer squares 190 of coverall material stitched to the inner surface of the coverall. Inner retainer squares 190 extend around the waist segment 166 and terminate behind the lumbar pad 192 as also shown in FIG. 14. The portions of straps 170, 172 extending between slits 186, 188 extend between the squares 190 and coverall 160 as shown in FIG. 16. Straps 170, 172 support the lumbar pad 192 which is secured by hook and loop connections 194, 196 respectively, as shown in FIG. 15. Hook strip 194 is attached to the back side of lumbar pad 192, and loop strips 194 are attached to the inside surface of the coverall 160. Besides being retained by hook and loop fasteners, the lumbar pad 192 is also held in place by a pad retainer square 198 made of coverall material which is stitched to the inside surface of the coverall 160 and covers the pad. Retainer square 192 is located in between the pad 192 and the wearer.

The method for activating and de-activating the support member 168 is identical to that described for the previous embodiment. The support member 168 of the coverall 160 includes buckles 200, 202, and 204 similar to the firefighter jacket for adjusting the tension of elastic straps 170, 172 which is dependent upon the waist size of the wearer.

Other closure means in all the embodiments may be used to adjust the support member to an activated configuration. For example, the hook and loop attachment panels may be replaced with other mechanical attachment mechanisms such as a perforated belt and buckle or a hook and D connection. However, the hook and loop connection is preferred because of the ease of attachment and removal.

While the forms of apparatus herein described constitute preferred embodiments of this invention, it is to be understood that the invention is not limited to these precise forms of apparatus, and that changes may be made therein without departing from the scope of the invention.

What is claimed is:

1. A jacket comprising:
   a torso portion having a waist segment covering a lower back area of a wearer; and
   means for supporting a lumbar region of a wearer, said support means being attached to said torso portion at said waist segment;
   said support means including,
      resilient means for urging said support means against said lumbar region, said resilient means including,
         elastic strap means extending through said waist portion and
         support closure means positioned adjacent to a frontal area of said garment and extending through said torso portion, for selectively activating said resilient means to urge said support means against said lumbar region, and deactivating said resilient means whereby said support means is not urged into said lumbar region, and
      a contact member attached to said elastic strap means and positioned to contact said lumbar region when said support means is activated.

2. The garment of claim 1 wherein said jacket includes a removable, insulated liner.

3. The garment of claim 2 wherein said jacket includes a front closure; and said support closure means is positioned adjacent to said front closure.

4. A garment comprising:
   a torso portion having a waist segment coverinq a lower back area of a wearer; and
   means for supporting a lumbar region of a wearer, said support means being attached to said torso portion at said waist segment; said support means including,
      resilient means for urging said support means against said lumbar region, said resilient means including support closure means extending through said torso portion, for selectively activating said resilient means to urge said support means against said lumbar region, and deactivating said resilient means whereby said support means is not urged into said lumbar region, said support closure means including first and second end portions which are releasably attachable to each other and to said garment such that said end portions are securable to said garment when said support means is in a deactivated configuration.

5. The garment of claim 4 wherein said end portions include means for releasable attachment to each other in overlapping relation.

6. The garment of claim 5 wherein said attachment means includes outer and inner panels of hook and loop fastener material.

7. The garment of claim 6 further comprising complementary panels of hook and loop fastener material at a frontal portion thereof and attachable to said inner panels for securing said end portions to said garment when said support means is in said deactivated configuration.

8. A work garment comprising:

a torso portion having a waist segment covering a lower back area of a wearer, a front closure and panels of hook and loop closure material adjacent said front closure;

elastic strap means attached to an inner surface of said torso portion and having end portions protruding from said torso portion adjacent said front closure, said end portions each having inner and outer hook and loop fastener material such that said end portions are attachable to each other in overlapping relation so that said strap means may be placed in an activated configuration, or a deactivated configuration in which said end portions are not attached to each other and are attached to said torso panels of hook and loop material; and a support pad of resilient material releasably attachable to said strap means at a rear portion of said torso portion by hook and loop fastener panels, said pad being positioned adjacent a lumbar area of a wearer, whereby said pad is urged into said lumbar area when said strap means is placed in said activated configuration, and is released from contact when said strap means is placed in said deactivated configuration.

* * * * *